Figure 1:
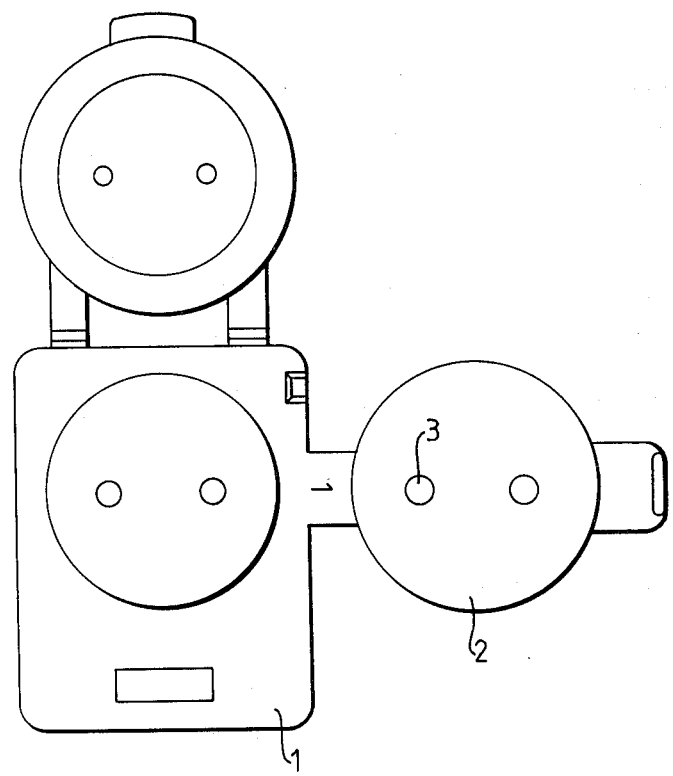

United States Patent [19]

Adlercreutz et al.

[11] 4,427,769
[45] Jan. 24, 1984

[54] IMMUNOASSAY FOR FECAL HUMAN HEMOGLOBIN

[75] Inventors: Herman Adlercreutz; Osmo A. Suovaniemi; Paul Partanen; Jueea I. Suni, all of Helsinki, Finland

[73] Assignee: Labsystems OY, Helsinki, Finland

[21] Appl. No.: 223,421

[22] Filed: Jan. 8, 1981

[30] Foreign Application Priority Data

Jan. 17, 1980 [FI] Finland .................................. 800140

[51] Int. Cl.$^3$ ...................... G01N 33/54; G01N 33/72
[52] U.S. Cl. ......................................... 435/7; 422/56; 422/61; 435/805; 436/66; 436/810
[58] Field of Search ...................... 435/7, 28, 188, 805, 435/810; 23/230 B, 913, 915, 931; 424/8, 12; 436/66

[56] References Cited

U.S. PATENT DOCUMENTS

| Re. 31,006 | 8/1982 | Schuurs et al. | 435/188 |
| 3,850,752 | 11/1974 | Schuurs et al. | 435/7 |
| 3,852,157 | 12/1974 | Rubenstein et al. | 435/7 |
| 4,092,120 | 5/1978 | Suovaniemi | 436/66 X |
| 4,292,403 | 9/1981 | Duermeyer | 435/7 |
| 4,333,734 | 6/1982 | Fleisher | 436/66 |

FOREIGN PATENT DOCUMENTS 54-150886 11/1979 Japan ..................................... 23/913

OTHER PUBLICATIONS

Grenett, et al., "Identification and Quantification of Sickle Cell Hemoglobin with an Enzyme-Linked Immunosorbent Assay (ELSIA)", *J. Lab. Clin. Med.*, vol. 96, No. 4, (1980), pp. 597-605.

Javid et al., "Radio-Ligand Immunoassay for Human Hemoglobin Variants", *J. Immunol. Meth.*, vol. 41, (1981), pp. 247-255.

Adlercreutz et al., "Evaluation of Fecatest, a New Guaiac Test for Occult Blood in Feces", *Clin. Chem.;* vol. 24, No. 5, (1978), pp 756-761.

Ostrow, "More on Relative Usefulness of Two Tests for Occult Blood in Stool", *Clin. Chem.*, vol. 25, No. 2, (1979), p. 338.

Guethlein et al., "Guaiaconic Acid and Diagnostic Agents Containing It", *Chem. Abstrs.*, vol. 90, No. 4, (1979), p. 352, Abstrs. No. 29017e.

*Primary Examiner*—Sidney Marantz
*Attorney, Agent, or Firm*—Hopgood, Calimafde, Kalil, Blaustein & Judlowe

[57] ABSTRACT

A method for the detection of hemoglobin or decomposition products of hemoglobin in feces. Human hemoglobin is isolated from the sample by means of an immunological reaction, i.e. a reaction between an antibody and an antigen, by using an antibody specific for human hemoglobin and attached to the solid phase. The human hemoglobin bound to the antibody is established hereupon.

5 Claims, 3 Drawing Figures

IMMUNOASSAY FOR FECAL HUMAN HEMOGLOBIN

The present invention is concerned with a method for the detection of hemoglobin or decomposition products of hemoglobin in feces.

Several methods are previously known for establishing fecal occult blood. A known method is based on the detection of the hemin liberated from hemoglobin in feces. The sample is placed onto a reagent paper containing guaiac resin. When hydrogen peroxide solution is added onto the reagent paper, the fecal hemin reacts in the way of peroxidase enzymes, the guaiac resin being oxidized into a blue compound. The strength of the colour formed depends on the concentration of hemoglobin in the sample. An apparatus suitable for the method, a so-called Fecatest package, is described in the U.S. Pat. No. 4,092,120. The said U.S. patent discloses a device for the storage and testing of laboratory samples. The device includes a base plate having an aperture therethrough and having a recess extending into its bottom surface. A first raised wall member extends outwardly from the upper surface of the base plate to define a sample storage area over the aperture. A top cover is configured to fit over the upper surface of the base plate and includes a raised portion which extends into the raised wall portion on the base plate to compress the sample. A bottom cover fits snugly within the recess on the bottom surface. A sheet of testing material such as filter paper may be disposed within the recess beneath the bottom cover where it is brought in contact with the sample through the aperture in the base plate.

The diagnostic preparations at present in use for detecting fecal occult blood cannot distinguish, e.g., between animal-based hemoglobin obtained from food containing meat and blood dishes and human hemoglobin. Likewise, peroxidase enzymes derived from plants, e.g. turnip and horseradish, produce an incorrect positive result in the test. The object of the present invention is to eliminate these disadvantages. In order to exclude sources of errors, according to the invention, the hemoglobin of human blood is "picked out" from the sample of feces specifically by immunological means.

In an immunological reaction an antigen reacts with the corresponding antibody and forms an immunological complex. One of the components can be bound into a solid phase, most appropriately some polymer, and the substance to be studied is in a solution, which is brought into contact with the component bound in the solid phase, whereby the formation of the complex takes place. A quantitative assay of the antigen or antibody to be studied can take place so that a certain quantity of an enzyme-stamped component is added to the reaction mixture, which component has the same immunological properties as the substance to be studied has. The binding of the enzyme-stamped component depends on the quantity of the substance to be studied. It follows from this that the enzyme activity either of the reaction solution obtained as the final result or of the solid phase can be used as the measure of the quantity of the substance to be studied. Such an enzyme-immuno-assay (EIA) is described, e.g., in the U.S. Pat. Nos. 3,654,090 and 4,016,043.

So far, an immunological method in which one of the components is bound in a solid phase has, however, not been used for the detection of fecal hemoglobin.

The method in accordance with the present invention is mainly characterized in that human hemoglobin is isolated from the sample by means of an immunological reaction, i.e. a reaction between an antibody and an antigen, by using an antibody specific for human hemoglobin and attached to the solid phase, and that the human hemoglobin bound to the antibody is established hereupon. This immunological method based on antigen detection is sufficiently sensitive to detect even very little quantities of hemoglobin or of its decomposition products.

By means of the method in accordance with the present invention, any blood occult in human feces is detected immunologically. The method is based on the use of a specific antibody. By its means, only hemoglobin derived from human being is detected.

An essential feature of the method is the use of anti-human-hemoglobin in order to "catch" any hemoglobin derived from human blood out of the sample.

In the reaction a certain appropriate buffer is used in order to elute the samples out of the absorbent used in the test. The immunological reaction itself is made "visible" by using an appropriate marker agent, such as another antibody having the same specificity as stamped with an appropriate enzyme or by using a solution containing guaiac resin, whereby the guaiac is oxidized into a blue compound in the presence of the heme of the hemoglobin (pseudo-peroxidase reaction).

Figure 2:
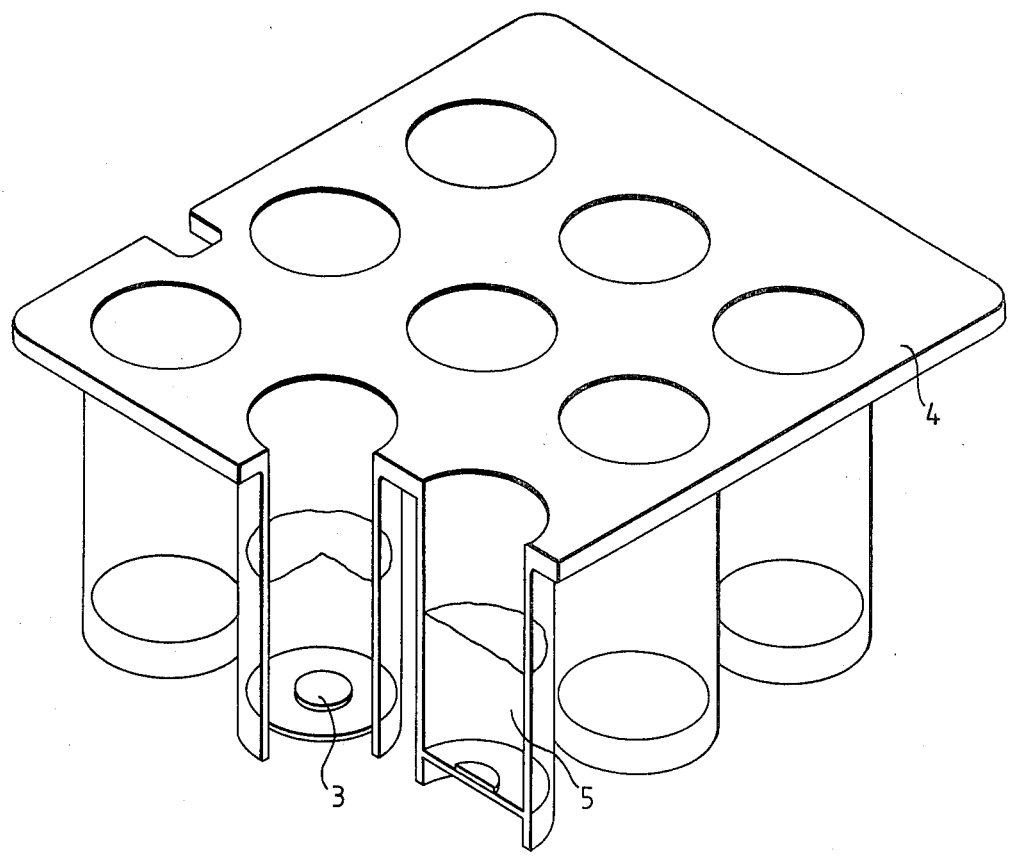
Figure 3:
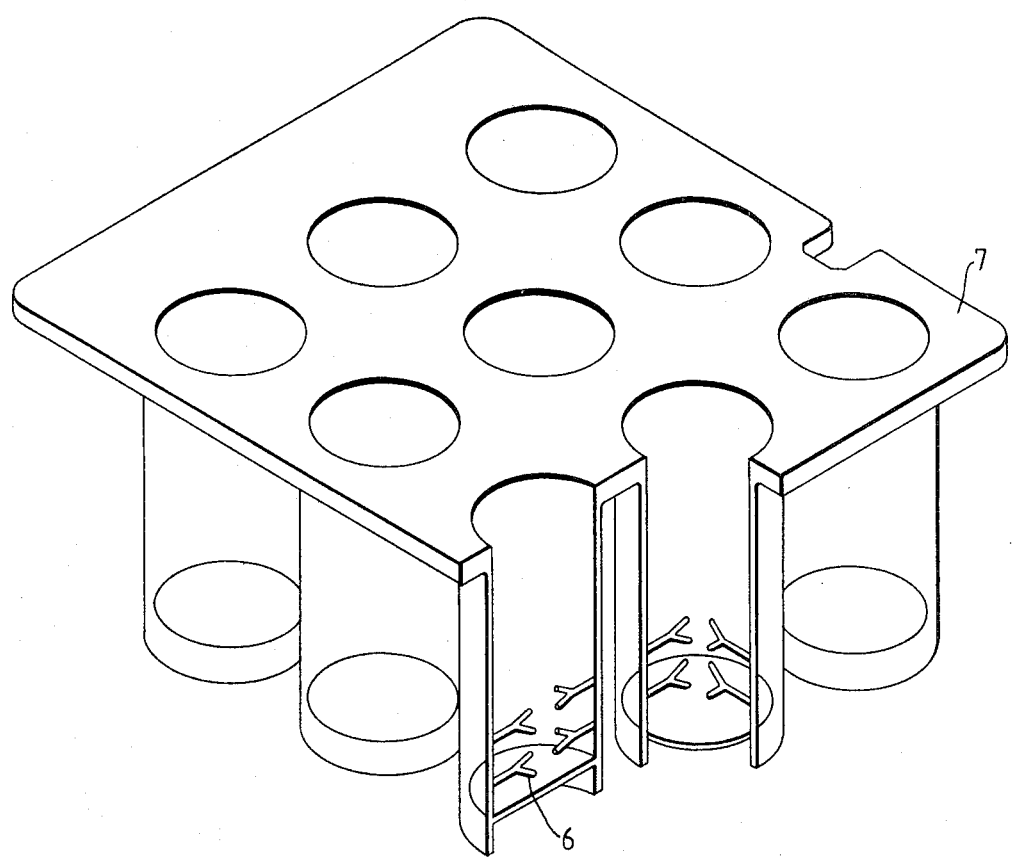

The invention will be described more closely below with reference to the attached drawings, wherein FIG. 1 shows a Fecatest device, in which the blood contained in feces can be absorbed into an absorbent, FIG. 2 shows the absorbent in the elution step, with the cuvette set used as the elution vessel partly in section, and FIG. 3 shows a cuvette set used in the immunological reaction, in which the antibody molecules bound to the walls of the cuvettes are, for the sake of illustration, shown as remarkably enlarged, with the cuvette set partly in section.

The equipment necessary for the method comprises a Fecatest package 1 (FIG. 1), into which the sample can be placed easily and hygienically. On the "laboratory side" 2 the Fecatest package has, e.g., filter paper (either one or several small ones or one larger one).

Into the Fecatest case, which has been specifically designed for hygienic transportation and testing of fecal samples, absorbent material 3 (e.g. filter paper) is added to the laboratory side, into which material the blood hemoglobin and/or decomposition products of same, possibly contained in the feces, are absorbed.

The absorbent is fastened to the Fecatest case so that it is placed between the guaiac-impregnated paper of the Fecatest and the plastics cover (laboratory side). In experiments that have been carried out it has been noticed that a sufficient quantity of hemoglobin or its decomposition product is carried from the feces sample through the paper containing guaiac resin into the next filter paper. Of course, some other type of positioning of the absorbent is also possible. The absorbent 3 is placed into the case so that it is easy to remove and to shift into some suitable vessel, e.g. set of cuvettes 4 (FIG. 2), for the elution of hemoglobin or its decomposition products.

The hemoglobin or its decomposition products derived from the sample and absorbed into the paper or any other porous absorbent material 2 can be eluted out of this material. From the eluate 5 it is possible to establish the hemoglobin by means of the enzyme-immunoassay method or by some other immune method. The absorbent can also be used as such in the immune tests.

When the hemoglobin is eluted out of the absorbent, a solution is obtained that contains hemoglobin (Hb) and other soluble molecules from the feces. When this solution is pipetted, e.g., into a cuvette of a polystyrene cuvette set 7(FIG. 3), onto whose walls and bottom a certain quantity of specific anti-human-hemoglobin 6 (anti-Hb) has been attached, an immunological reaction, ab-ag reaction, takes place between the antibody, i.e. anti-Hb, and the antigen, i.e. the Hb in the sample. In this way the Hb in the sample is bound to this solid phase (IgG, i.e., immunoglobulin G fraction).

After a certain incubation time (= the time taken by the immunological reaction) the cuvette 7 (solid phase) is washed highly carefully in order to remove all unbound material. Of course, the solid phase may be even highly different from that indicated in the example. It may be a polymer totally different from polystyrene, and likewise its shape may be completely different from a cuvette or vessel, e.g. a ball, ring, disk, etc.

In the next step the objective is to be able to ascertain the taking place of the immunological reaction, i.e. whether something has been bound from the sample to the anti-human-hemoglobin, which was in the solid phase, or not.

Afterwards, it is possible to ascertain the taking place of the reaction, for example, by the following means:

1. After the sample has been bound to the antibody attached to the solid phase in the cuvette and after the cuvette has been washed, a certain quantity of the IgG of anti-human-Hb is added to the cuvette, to which IgG some enzyme has been conjugated as a marker. The binding of the enzyme-marked IgG to the antibody in the solid phase depends on how much there is "free antibody" in the solid phase after the treatment of the sample. Thus, by means of the enzyme stamp it is possible to ascertain the reaction of the antibody (anti-human-Hb) and the antigen (human Hb) by addition of a substrate specific for the enzyme concerned, whereby the enzyme splits from the substrate a coloured, visually or photometrically readable compound. A so-called "Sandwich" technique of corresponding type in connection with the EIA method has been described, e.g., in the above U.S. Pat. No. 4,016,043. The quantity of the enzyme can be established either by measuring the quantity bound to the solid phase or by measuring the quantity that has remained free in the solution.

2. Another alternative of performance of the enzyme reaction is to add, at the same time with the sample, a known quantity of a conjugate, i.e. enzyme-stamped human Hb, whereby both the Hb in the sample and the added Hb compete with the antibody, i.e. anti-Hb, in the solid phase. The immunological reaction (ab-ag reaction) can be made visible by adding a substrate specific for the enzyme of the conjugate, from which substrate a coloured compound is split. A corresponding so-called competitive EIA-test is described, e.g., in the above U.S. Pat. No. 3,654,090.

3. As an alternative of an enzyme reaction, it is possible to use the guaiac reaction. After the sample has reacted with the anti-Hb in the solid phase and the cuvette has been washed, a known quantity of guaiac is added into the cuvette. If the sample has contained human hemoglobin, which has been bound to its specific antibody on the walls of the cuvette, a pseudo-peroxidase reaction takes place, i.e. the guaiac is oxidated into a blue compound in the presence of a hydrogen peroxide, which blue compound can be measured photometrically. The strength of the blue colour is proportional to the quantity of human hemoglobin in the sample. Thus, in this alternative, the enzyme reaction necessary in EIA is not used. Nevertheless, owing to the use of specific antibody, only the human hemoglobin can be measured.

An embodiment of the invention will be described in the following example, to which the invention is, however, not restricted.

(1) The absorbent containing the sample is taken from the laboratory-side cover of the Fecatest case and placed, e.g., into a FP-9 cuvette.
(2) The FP-9 cuvette of polystyrene was "sensitized" in advance with the anti-human-hemoglobin-IgG-fraction.
(3) 200 μl of saline solution buffered with phosphate (0.1 M PBS, pH 7.4) is added to the cuvette.
(4) Incubation, e.g., for 2 hours at +37° C.
(5) The cuvette is washed with 400 μl of distilled water.
(6) 200 μl of anti-human-Hb-IgG-fraction (PBS as the diluting liquid) stamped with some suitable enzyme (e.g. alkaline phosphatase) is added into the cuvette (addition of conjugate).
(7) Incubation, e.g., for 2 hours at +37° C.
(8) Is washed as in section (5).
(9) A substrate specific for the enzyme used in the conjugate is added (in the example used, paranitrophenylphosphate).
(10) After incubation of 30 minutes (= enzyme reaction) (at +37°) 200 μl of an appropriate solution is added in order to stop the reaction (in this particular example, 0.1 M/NaOH).
(11) The result is either measured photometrically or read visually.

The reaction can also be performed in many other ways. The example given is only one out of many enzyme-immuno-methods that have been found to be good. The incubation times, volumes of reaction mixtures, "enzyme stamps", and solid-phase conditions may vary.

The absorbent in the Fecatest case may contain a specific antibody (anti-human-hemoglobin) bound by means of a chemical bond, whereby the antigen (i.e. the human hemoglobin or its decomposition products) is bound specifically right at this stage. In such a case the absorbent concerned is used as the solid phase. The process is continued by after the washings adding the conjugate, and after a certain incubation and washings the substrate is added, and the final result is read visually or possibly by means of a densitometer.

What we claim is:

1. A method for the specific detection of human hemoglobin in feces comprising
   (a) contacting a sample of said feces with one side of a guaiac-impregnated filter paper which in turn is contacted on its other side by an absorbent for said hemoglobin, such that hemoglobin is absorbed into said absorbent,
   (b) eluting said absorbed hemoglobin from said absorbent,
   (c) reacting said eluted hemoglobin with a specific anti-human hemoglobin antibody to form a complex, and
   (d) quantifying the amount of human hemoglobin complexed with said antibody.

2. The method of claim 1 wherein said absorbtion and said reaction are carried out substantially simultaneously such that said hemoglobin reacts substantially simultaneously with said specific anti-human-hemoglobin antibody which is bound to said absorbent material.

3. The method of claim 2 wherein the amount of said human hemoglobin which is complexed with said specific antibody is further treated by reacting it with a solution containing guaiac resin which is oxidized by hydrogen peroxide to form a blue coloured compound.

4. The method of claim 1 wherein said specific anti-human hemoglobin antibody has been bound to a solid phase surface.

5. The method of claim 4 wherein said human hemoglobin which is complexed with said specific antibody is further treated by
   (a) adding to said complex a measured amount of either enzyme labeled human hemoglobin or enzyme labeled anti-human-hemoglobin antibody, and
   (b) determining the enzymatic activity of either the solid phase or the resultant solution, such that the amount of said complex is quantified.

* * * * *